(12) United States Patent
Soro et al.

(10) Patent No.: US 9,655,533 B2
(45) Date of Patent: May 23, 2017

(54) SYSTEM AND METHOD FOR LOW POWER SAMPLING OF PLETHYSMOGRAPH SIGNALS

(71) Applicant: General Electric Company, Schenectady, NY (US)

(72) Inventors: Stanislava Soro, Niskayuna, NY (US); SM Shajedul Hasan, Rexford, NY (US); Jason Harris Karp, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 684 days.

(21) Appl. No.: 14/078,582

(22) Filed: Nov. 13, 2013

(65) Prior Publication Data

US 2015/0133801 A1    May 14, 2015

(51) Int. Cl.
| | |
|---|---|
| *A61B 5/02* | (2006.01) |
| *A61B 5/0295* | (2006.01) |
| *A61B 5/00* | (2006.01) |
| *A61B 5/024* | (2006.01) |
| *A61B 5/026* | (2006.01) |

(52) U.S. Cl.
CPC ........ *A61B 5/0295* (2013.01); *A61B 5/02028* (2013.01); *A61B 5/02416* (2013.01); *A61B 5/7285* (2013.01); *A61B 5/0261* (2013.01)

(58) Field of Classification Search
CPC .. A61B 5/02416; A61B 5/0295; A61B 5/7285
See application file for complete search history.

(56) References Cited

U.S. PATENT DOCUMENTS

| | | |
|---|---|---|
| 6,616,613 B1 | 9/2003 | Goodman |
| 7,447,541 B2 | 11/2008 | Huiku et al. |

(Continued)

FOREIGN PATENT DOCUMENTS

| | | |
|---|---|---|
| EP | 0298620 A1 | 1/1989 |
| WO | 2004026132 A2 | 4/2004 |

OTHER PUBLICATIONS

Baheti et al., "An ultra low power pulse oximeter sensor based on compressed sensing", Body Sensor Networks, 2009, pp. 144-148.

(Continued)

*Primary Examiner* — Jacqueline Cheng
*Assistant Examiner* — Angeline Premraj
(74) *Attorney, Agent, or Firm* — Pabitra K. Chakrabarti

(57) ABSTRACT

A method for generating a sampled plethysmograph data, includes measuring a plethysmograph waveform indicative of a first cardiac cycle and a second cardiac cycle, each cycle including a systolic waveform and a diastolic waveform. The method further includes estimating a first start time and a first duration for the systolic waveform of the first cardiac cycle and computing a plurality of amplitudes at a plurality of time instants for the first duration. The method further includes determining a second start time and a second duration of the systolic waveform of the second cardiac cycle. The method also includes assigning the second cardiac cycle, the second start time, and the second duration to the first cardiac cycle, the first start time, and the first duration respectively. The method further includes iteratively performing the steps of measuring, estimating, computing, determining and assigning for the plurality of cardiac cycles acquired sequentially in time.

28 Claims, 11 Drawing Sheets

(56) References Cited

U.S. PATENT DOCUMENTS

| | | |
|---|---|---|
| 8,073,516 B2 | 12/2011 | Scharf et al. |
| 8,221,326 B2 | 7/2012 | Baker, Jr. |
| 8,425,415 B2 | 4/2013 | Tran |
| 2012/0053432 A1 | 3/2012 | Huiku et al. |

OTHER PUBLICATIONS

Soni et al., "Delineation of Raw Plethysmograph using Wavelets for Mobile based Pulse Oximeters", Proceedings of 5th Innovative Conference on Embedded Systems, Mobile Communication and Computing, Nov. 2010, pp. 74-84.

SYSTEM AND METHOD FOR LOW POWER SAMPLING OF PLETHYSMOGRAPH SIGNALS

BACKGROUND

This specification relates generally to sampling of signals. More particularly, this specification relates to for low power sampling of plethysmograph signals.

Pulse oximeter is an instrument to determine concentration of oxygen in the blood flowing through the peripheral arteries (i.e. arteries that are farthest from the heart). The measure of oxygen in the peripheral arteries is referred to as 'Saturation of Peripheral Oxygen' abbreviated as $SPO_2$ and expressed in percentage values. Pulse oximeter determines $SPO_2$ based on a ratio of amount of red (wavelength 600-750 nm) and infrared (wavelength 850-1000 nm) light energy transmitted through (or reflected from) the peripheral arteries. Pulse oximeter enables instantaneous in-vivo measurements of arterial oxygenation as well as heart rate and perfusion signals, and thereby provides an early warning of arterial hypoxemia, for example Low power consumption is a pre-requisite for portable and wearable medical sensors which allow the subject to move freely. In the case of pulse oximeter, the power consumption is largely due to the power requirement of the light sources (LEDs), which are normally driven continuously at a high rate. Conventional techniques available for reducing the power consumption of the LEDs are based on reduction of the amplitude and/or width of the LED pulses. Further, sampling rates lower than the Nyquist rate of the plethysmograph signal may be employed to reduce the LED power. However, such techniques require additional signal processing tasks such as signal-to-noise ratio measurements and sophisticated reconstruction algorithms which are computationally complex.

There is a need for an enhanced low power sampling of plethysmograph signals.

BRIEF DESCRIPTION

In accordance with one aspect of the present technique, a method is disclosed. The method includes measuring a plethysmograph waveform indicative of a plurality of cardiac cycles. The plethysmograph waveform includes a systolic waveform and a diastolic waveform, corresponding to each cardiac cycle. The method further includes estimating a first start time and a first duration for the systolic waveform of a first cardiac cycle, based on at least one cardiac cycle from the plurality of cardiac cycles. The method also includes computing a plurality of amplitudes at a plurality of time instants for the first duration of the systolic waveform of the first cardiac cycle. The method further includes determining a second start time and a second duration of the systolic waveform of a second cardiac cycle from the plurality of cardiac cycles based on the plurality of amplitudes. The second cardiac cycle is acquired after the first cardiac cycle in time sequence. The method also includes assigning the second cardiac cycle, the second start time, and the second duration to the first cardiac cycle, the first start time, and the first duration respectively. The method further includes iteratively performing the steps of measuring, estimating, computing, determining and assigning for the plurality of cardiac cycles acquired sequentially in time to generate a sampled plethysmograph data.

In accordance with another aspect of the present technique, a system is disclosed. The system includes a sensor configured to measure a plethysmograph waveform indicative of a plurality of cardiac cycles. The plethysmograph waveform includes a systolic waveform and a diastolic waveform corresponding to each cardiac cycle. The system further includes a timing module communicatively coupled to the sensor and configured to estimate a first start time and a first duration for the systolic waveform of a first cardiac cycle, based on at least one cardiac cycle from the plurality of cardiac cycles. The system also includes a sampling module communicatively coupled to the timing module and the sensor. The sampling module is configured to compute a plurality of amplitudes at a plurality of time instants for the first duration of the systolic waveform of the first cardiac cycle. The system further includes a processing module communicatively coupled to the sampling module and the timing module. The processing module is configured to receive the plurality of amplitudes from the sampling module and determine a second start time and a second duration of the systolic waveform of a second cardiac cycle from the plurality of cardiac cycles, based on the plurality of amplitudes. The second cardiac cycle is generated after the first cardiac cycle in time sequence. The processing module of the system is also configured to assign the second cardiac cycle, the second start time, and the second duration to the first cardiac cycle, the first start time, and the first duration respectively. The processing module of the system is configured to iteratively perform receiving, determining and assigning steps for the plurality of cardiac cycles generated sequentially in time to generate a sampled plethysmograph data.

In accordance with another aspect of the present technique, a method is disclosed. The method includes generating a plethysmograph waveform indicative of a plurality of cardiac cycles. The plethysmograph waveform includes a systolic waveform and a diastolic waveform, corresponding to each cardiac cycle. The method also includes estimating a first start time and a first duration for the systolic waveform of a first cardiac cycle, based on at least one cardiac cycle from the plurality of cardiac cycles. The method further includes computing a plurality of amplitudes at a plurality of time instants for the first duration of the systolic waveform of the first cardiac cycle. The method also includes determining a second start time and a second duration of the systolic waveform of a second cardiac cycle from the plurality of cardiac cycles based on the first plurality of amplitudes. The second cardiac cycle is generated after the first cardiac cycle in time sequence. The method further includes reconstructing a plurality of diastolic amplitudes corresponding to the diastolic waveform of the first cardiac cycle based on the plurality of amplitudes. The method further includes assigning the second cardiac cycle, the second start time, and the second duration to the first cardiac cycle, the first start time, and the second duration respectively. Finally, the method includes iteratively performing computing, determining, reconstructing and assigning steps for the plurality of cardiac cycles generated sequentially in time to generate a sampled plethysmograph data.

DRAWINGS

These and other features and aspects of embodiments of the present specification will become better understood when the following detailed description is read with reference to the accompanying drawings in which like characters represent like parts throughout the drawings, wherein.

DETAILED DESCRIPTION

Embodiments of the present specification relate to a system and a method for determining a plurality of amplitudes corresponding to a sampled plethysmograph data. Specifically, in certain embodiments, a plethysmograph waveform indicative of a plurality of cardiac cycles is generated. Each cardiac cycle of the plethysmograph waveform includes a systolic waveform and a diastolic waveform. A first start time and a first duration of the systolic waveform of a first cardiac cycle are estimated based on at least one cardiac cycle from the plurality of cardiac cycles. Estimating the first duration involves determining an average value of the plurality of cardiac cycles and deriving the first start time and the first duration based on the average value. A plurality of amplitudes at a plurality of time instants of the first duration of the systolic waveform of the first cardiac cycle is then computed. A second start time and a second duration of the systolic waveform of a second cardiac cycle from the plurality of cardiac cycles, are determined based on the plurality of amplitudes. The second cardiac cycle referred herein is generated after the first cardiac cycle in time sequence. The computation of the plurality of amplitudes of the first cardiac cycle, determining of the second start time and the second duration of the second cardiac cycle are performed for the plurality of cardiac cycles generated sequentially in time to generate a sampled plethysmograph data.

Figure 1:
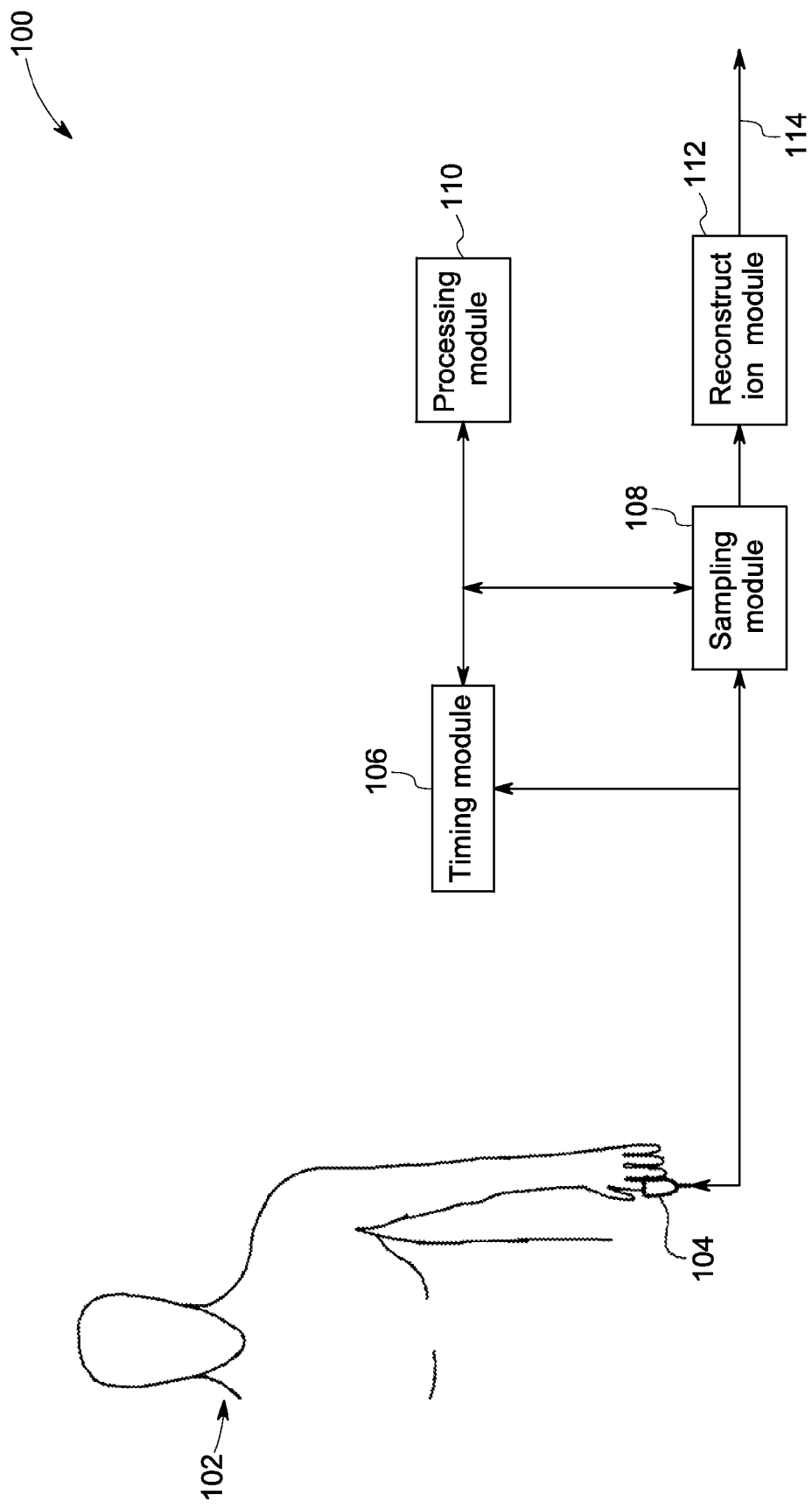
FIG. 1 is a block diagram illustrating a system for low power sampling of plethysmograph signals in accordance with an exemplary embodiment.

FIG. 1 is a block diagram of a system 100 used for low power sampling of plethysmograph signals in accordance with an exemplary embodiment. Specifically, the system 100 is used for generating a sampled plethysmograph data from a subject 102. The system 100 includes a sensor 104, a timing module 106, a sampling module 108, a processing module 110 and a reconstruction module 112.

In the illustrated embodiment, the sensor 104 is coupled to a peripheral artery of the subject 102 and configured to generate a plethysmograph waveform from the subject 102. The sensor 104 includes an emitter (LED, OLED, laser diode, etc.) for emitting a red light and another emitter for emitting an infrared light. The peripheral artery may be in a finger, a toe, ear, nose, forehead or other tissue sites on the subject 102. The light from the red and infrared light sources are emitted to the peripheral artery sources to capture the plethysmograph waveform created by the volumetric change of blood flowing through the peripheral artery. Specifically, the sensor 104 is configured to measure a plethysmograph waveform indicative of a plurality of cardiac cycles. The plethysmograph waveform includes a systolic waveform and a diastolic waveform corresponding to each cardiac cycle.

The timing module 106 is communicatively coupled to the sensor 104. The timing module 106 provides timing signals to the sensor 104 for switching on and off the light sources. The timing module 106 is configured to estimate a first time and a first duration of the systolic waveform of a first cardiac cycle, based on at least one cardiac cycle from the plurality of cardiac cycles. The timing module 106 is further configured to determine an average value of the plurality of cardiac cycles and estimate the first start time and the first duration based on the average value. In one embodiment, the timing module 106 is a hardware component. The timing module 106 may include timing circuitry and a plurality of computing elements configured to generate the timing signals. In another embodiment, the timing module 106 is stored in a memory and executed by at least one processor.

The sampling module 108 is communicatively coupled to the sensor 104 and the timing module 106. The sampling module 108 is configured to receive the plethysmograph waveform from the sensor 104 and the timing signals from the timing module 106. The sampling module 108 is configured to perform sampling of the plethysmograph waveform. The sampling module 108 computes a plurality of amplitudes at a plurality of time instants for the first duration of the systolic waveform of the first cardiac cycle. In one embodiment, the sampling module 108 is a customized hardware module. In another embodiment, the sampling module 108 is stored in the memory and executable by at least one processor.

The processing module 110 is communicatively coupled to the timing module 106 and the sampling module 108. The processing module 110 is configured to receive the plurality of amplitudes from the sampling module 108 and determine a second start time and a second duration of the systolic waveform of a second cardiac cycle from the plurality of cardiac cycles, based on the plurality of amplitudes. The processing module 110 is further configured to assign the second cardiac cycle, the second start time, and the second duration to the first cardiac cycle, the first start time, and the first duration respectively. The processing module 110 is also further configured to process the plurality of cardiac cycles generated sequentially in time to generate a sampled plethysmograph data. The processing module 110 may include at least one processor and a memory (not shown).

At least one processor of the processing module 110 may include at least one arithmetic logic unit, microprocessor, general purpose controller or other processor arrays to perform the desired computations. The processing capability of at least one processor, in one example, may be limited to reception of the sampled plethysmograph data. The processing capability of at least one processor, in another example, may include performing more complex tasks such as estimating a duration of a cardiac cycle and a start time instant of a systolic waveform, or the like. In other embodiments, other type of processors, operating systems, and physical configurations are also envisioned. In certain embodiments, the processing module 110 may include the timing module 106, and the sampling module 108.

In one embodiment, the processing module 110 may also include at least one memory module. In another embodiment, the processing module 110 is communicatively coupled to at least one memory module. The memory module may be a non-transitory storage medium. For example, the memory module may be a dynamic random access memory (DRAM) device, a static random access memory (SRAM) device, flash memory or other memory devices. In one embodiment, the memory module may include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. In one specific embodiment, the non-transitory computer readable medium may be encoded with a program to instruct at least one processor to generate the sampled plethysmograph data.

The reconstruction module 112 is communicatively coupled to the sampling module 108 and configured to generate an entire cardiac cycle based on the plurality of amplitudes generated from the sampling module 108. The term "entire cardiac cycle" mentioned herein refers to a plurality of systolic amplitudes corresponding to a systolic waveform of the cardiac cycle and a plurality of diastolic amplitudes corresponding to a diastolic waveform of the cardiac cycle. In one embodiment, the reconstruction module 112 is a custom hardware module. In another embodiment, the reconstruction module 112 is stored in a memory and executable by at least one processor. In yet another embodiment, the reconstruction module 112 may be integrated with the processing module 110. The reconstruction module 112 is further configured to process the sampled plethysmograph data corresponding to the systolic waveform of the first cardiac cycle and generate a plurality of amplitudes of the diastolic waveform of the first cardiac cycle. The reconstruction module 112 is configured to generate a plurality of amplitudes 114 of the entire cardiac cycle.

Figure 2:
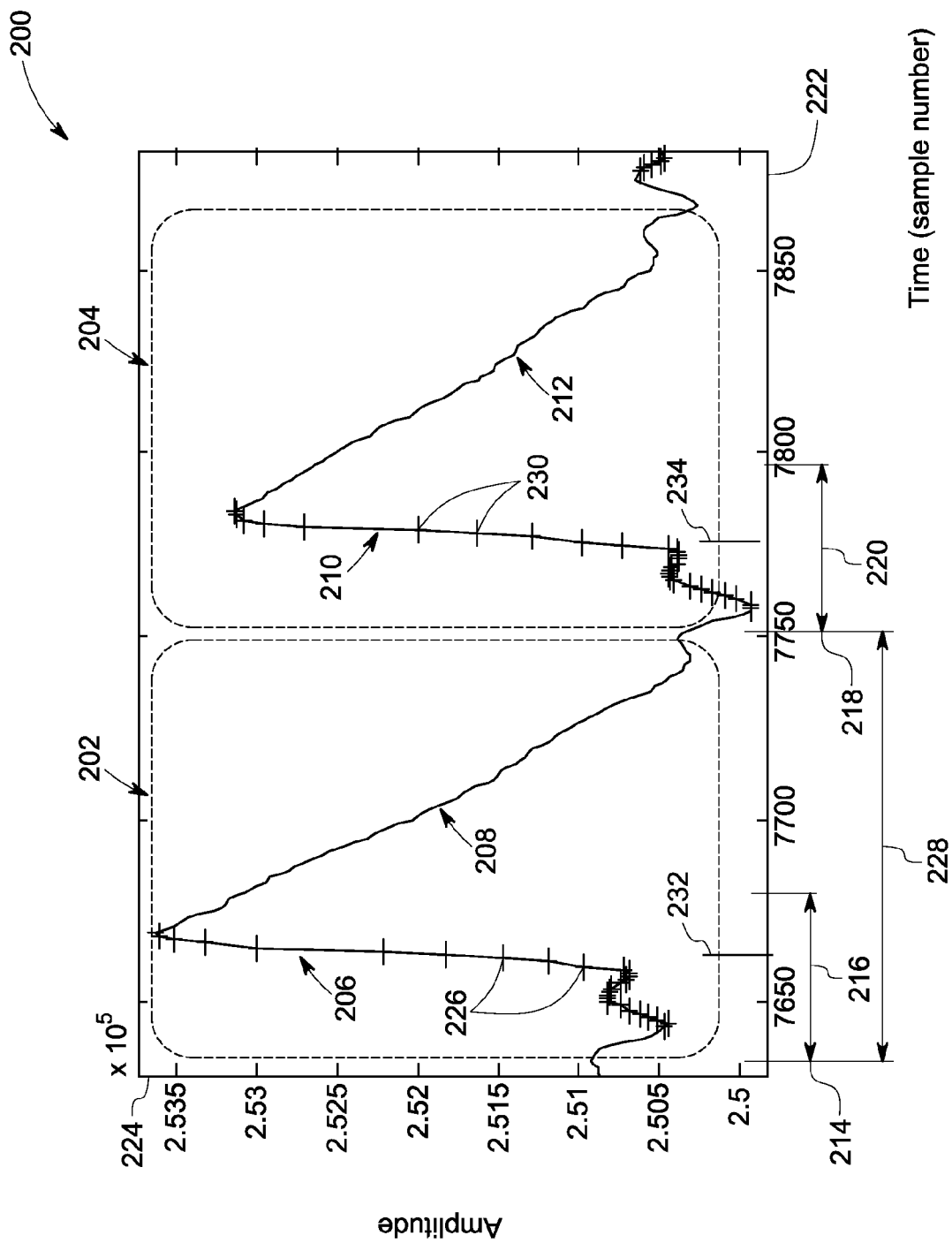
FIG. 2 is a graph representative of a plethysmograph waveform having two successive cardiac cycles in accordance with an exemplary embodiment.

FIG. 2 is a graph representative of a plethysmograph waveform 200 having two successive cardiac cycles 202, 204 among a plurality of cardiac cycles in accordance with an exemplary embodiment. The x-axis 222 of the graph 200 is representative of time and the y-axis 224 is representative of magnitude of the plethysmograph waveform 200. The plethysmograph waveform 200 includes the first cardiac cycle 202 and the second cardiac cycle 204. In the illustrated embodiment, the second cardiac cycle 204 is generated after the first cardiac cycle 202 in time sequence. Each cardiac cycle has a systolic waveform and a diastolic waveform. In the illustrated embodiment, the first cardiac cycle 202 has a systolic waveform 206 and a diastolic waveform 208. The second cardiac cycle 204 has a systolic waveform 210 and a diastolic waveform 212. The systolic waveform 206 of the first cardiac cycle 202 has a first start time 214 and a first duration 216. The first cardiac cycle 202 has an entire duration 228 including the first duration 216 and a duration (not shown) corresponding to the diastolic waveform 208. The systolic waveform 210 has a second start time 218 and a second duration 220. The systolic waveform 206 of the first cardiac cycle 202 has a start time 232 and the systolic waveform 210 of the second cardiac cycle 204 has a start time 234.

In the illustrated embodiment, a plurality of amplitudes 226 are determined by sampling the plethysmograph waveform 200 for the first duration 216 from the first start time 214. The processing module is configured to identify a portion of the first cardiac cycle 202, which occurs within the first duration 216. The identification of the portion of the first cardiac cycle 202 occurring within the first duration 216, involves processing the plurality of amplitude 226 within the first duration 216. In the illustrated embodiment, the systolic waveform 206 is the identified portion of the first cardiac cycle 202 occurring within the first duration 216. Further, the second start time 218 and the second duration 220 of the second cardiac cycle 204 are determined based on the identified portion of the first cardiac cycle 202. Further, a plurality of amplitudes 230 are determined by sampling the plethysmograph waveform 200 for the second duration 220 from the second start time 218. The identification of a portion of the second cardiac cycle 204 occurring within the second duration 220, involves processing the plurality of amplitudes 230 within the second duration 220. In the illustrated embodiment, the systolic waveform 210 is the identified portion of the second cardiac cycle 204 occurring within the second duration 220. Since, the red and infrared emitters are powered "ON" during the sampling period, the power required for operating the sources is reduced. The processing of the plurality of amplitudes 226 and identification of the portion of the first cardiac cycle 202 are explained in greater detail with reference to subsequent figures.

Further, a second start time 218 is estimated corresponding to the second cardiac cycle 204. Determination of the second start time 218 involves determining the start time 232 of the systolic waveform 206. The start time 232 is a time instant among the plurality of time instants corresponding to the plurality of amplitudes 226. The start time 234 of the systolic waveform 210 is determined by adding the entire duration 228 to the start time 232. The start time 234 of the systolic waveform 210 of the second cardiac cycle 204 is assigned to the second start time 218. In some embodiments, the plurality of time instants 226 may not include the start time 232 of the systolic waveform 206. In such embodiments, the second start time 218 is assigned with a value equal to the entire duration 228 added to the first start time 214.

Figure 3:
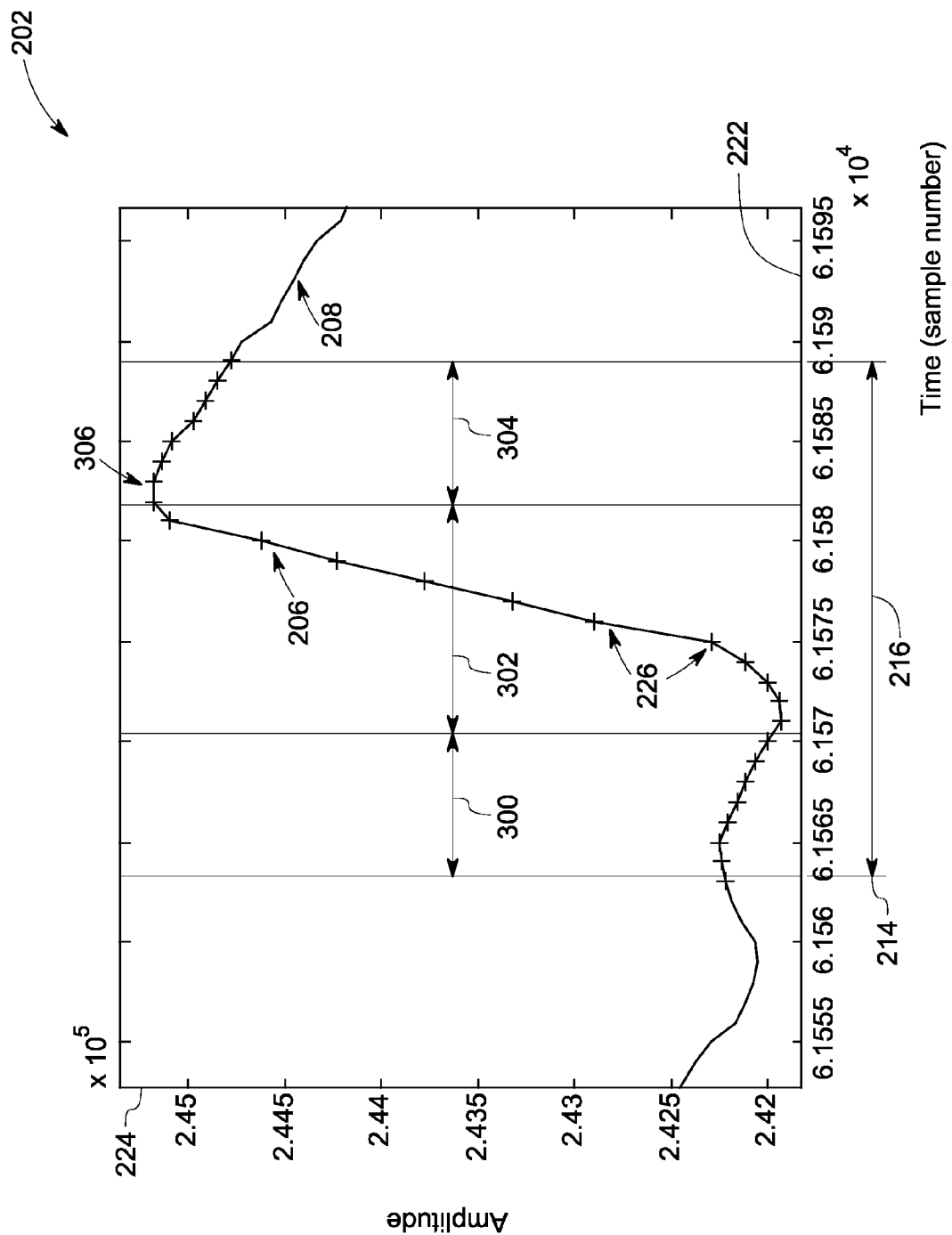
FIG. 3 is a graph representative of a systolic waveform of a first cardiac cycle in accordance with an exemplary embodiment.

FIG. 3 is a graph representative of the systolic waveform 206 indicative of the first cardiac cycle 202 of the plethysmograph waveform in accordance with an exemplary embodiment of FIG. 2. The graph has the x-axis 222 representative of time and a y-axis 224 representative of amplitude of the plethysmograph waveform. The first cardiac cycle has the first start time 214 and the first duration 216. The first duration 216 includes a systolic rise duration 302, a first offset duration 300 before the systolic rise duration 302 and a second offset duration 304 after the systolic rise duration 302. The first offset duration 300 and the second offset duration 304 are determined to compensate for any variations between the plurality of cardiac cycles. In one embodiment, the first offset duration 300 and the second offset duration 304 has 5-8 samples and the systolic rise duration 302 includes about 10-12 samples. In alternate embodiments, first offset duration 300 and the second offset duration 304 may vary.

The first start time 214 and the first duration 216 are determined such that the systolic waveform 206 occurs within the systolic rise duration 302. In some embodiments, the systolic waveform 206 does not occur within the systolic rise duration 302. In such embodiments, the systolic waveform 206 may occur within the first duration 216. If the systolic waveform 206 occurs before the systolic rise duration 302, the first offset duration 300 includes an initial portion of the systolic waveform 206. If the systolic waveform 206 occurs beyond the systolic rise duration 302, the second offset duration 304 includes a remaining portion of the systolic waveform 206.

Although in the illustrated graph, the first start time 214 coincides with a start of the first offset duration 300, it should not be interpreted as a limitation of the technique. The first start time 214 may coincide with any point on the first cardiac cycle 202. In the illustrated embodiment, the systolic rise duration 302 includes the systolic waveform 206. In another embodiment, the systolic rise duration 302 may not include the systolic waveform 206. The first duration 216 may correspond to a portion of the systolic waveform 206, a portion of the diastolic waveform 208, or a combination thereof. The first duration 216 may be assigned different values for successive cardiac cycles of the plethysmograph waveform. For one cardiac cycle, the first duration 216 may have a smaller value compared to the duration of the systolic rise. For another cardiac cycle, the first duration may have a value equal to an average duration of the entire corresponding cardiac cycle.

In an exemplary embodiment, the plurality of amplitudes 226 are processed to determine a portion of the first cardiac cycle 202, within the first duration 216. The processing involves determining a peak value 306 among the plurality of amplitudes 226. The processing also involves determining a pattern of the plurality of amplitudes 226. In the illustrated embodiment, for example, the pattern of the plurality of amplitudes 226 is a rising pattern. In other embodiments, a pattern of the plurality of amplitudes 226 may be a falling pattern, an oscillating pattern and the like. In the illustrated embodiment, the identified portion of the first cardiac cycle 202 is the systolic waveform 206. In other embodiments where other patterns are determined, the identified portion of the first cardiac cycle 202 may be the diastolic waveform 208, a portion of the systolic waveform 206, or a portion of the diastolic waveform 208. The second start time and the second duration are determined based on the identified portion of the first cardiac cycle 202, the first start time 214, and the first duration 216. The determination of the second start time and the second duration are explained in greater detail with reference to subsequent figures.

Figure 4:
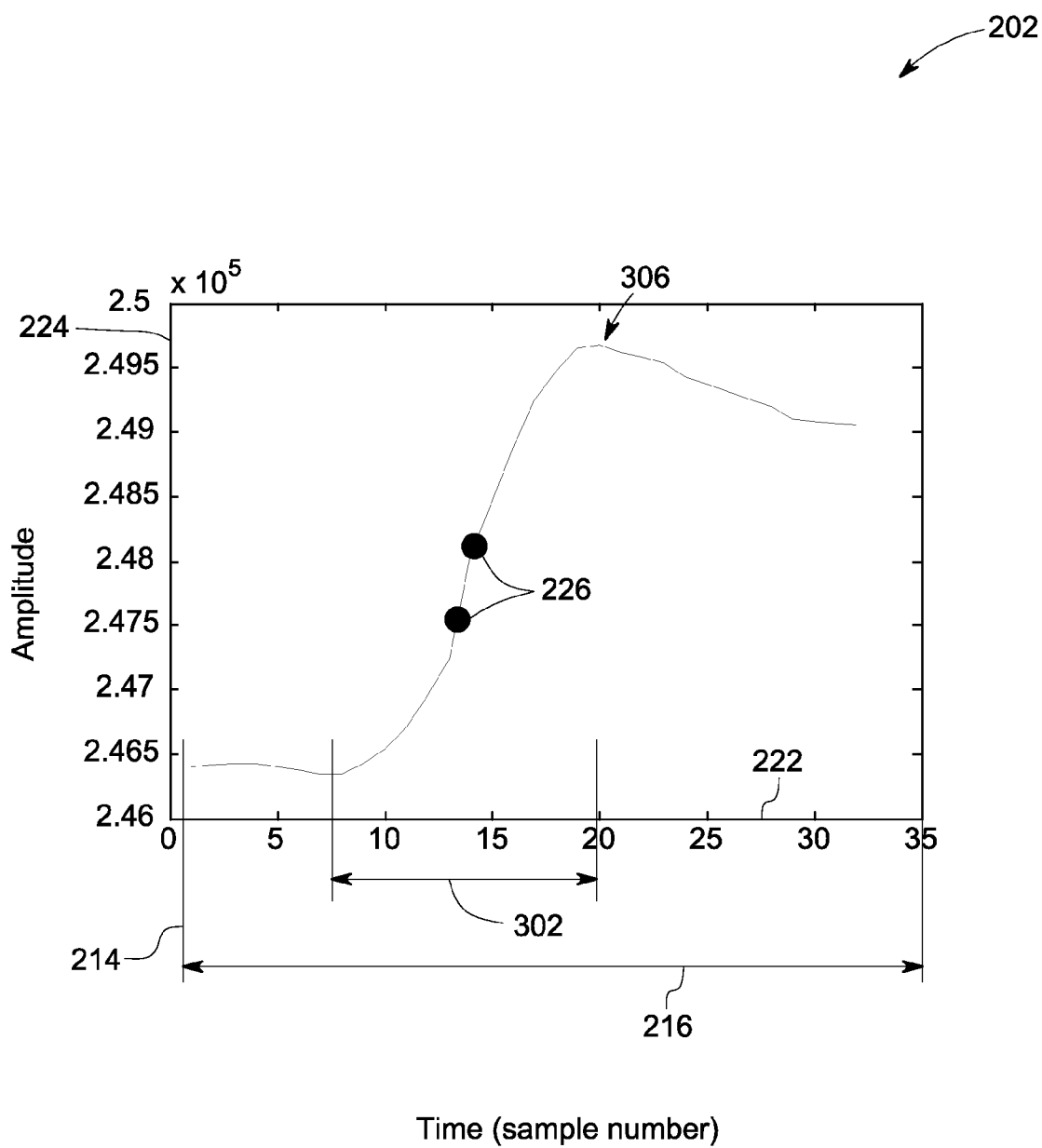
FIGS. 4-8 are graphs illustrating identified portions of a first cardiac cycle among a plurality of cardiac cycles in accordance with an exemplary embodiment.

FIG. 4 is a graph representative of the identified portion of the first cardiac cycle 202 of the plethysmograph waveform, corresponding to the first duration 216 in accordance with an exemplary embodiment of FIG. 3. The x-axis 222 is representative of time and the y-axis 224 is representative of the amplitude. The first start time 214 corresponds to "zero" value on the x-axis 222 and the first duration 216 corresponds to the entire x-axis 222. The identified portion of the first cardiac cycle 202 includes the systolic waveform 206 occurring in the systolic rise duration 302 of the first cardiac cycle 202. In such an embodiment, a threshold for determining the peak amplitude 306 is estimated based on the plurality of amplitudes 226.

In an alternate embodiment, the identified portion of the first cardiac cycle 202 includes the systolic waveform 206 and also at least a portion of the diastolic waveform 208. The identified portion occurs within the systolic rise duration 302. In such an embodiment, a first value less than the first duration 216, is assigned to the second duration. Assigning the first value less than the first duration 216, to the second duration facilitates to restrict the sampling process to the systolic waveform of the second cardiac cycle.

Figure 5:
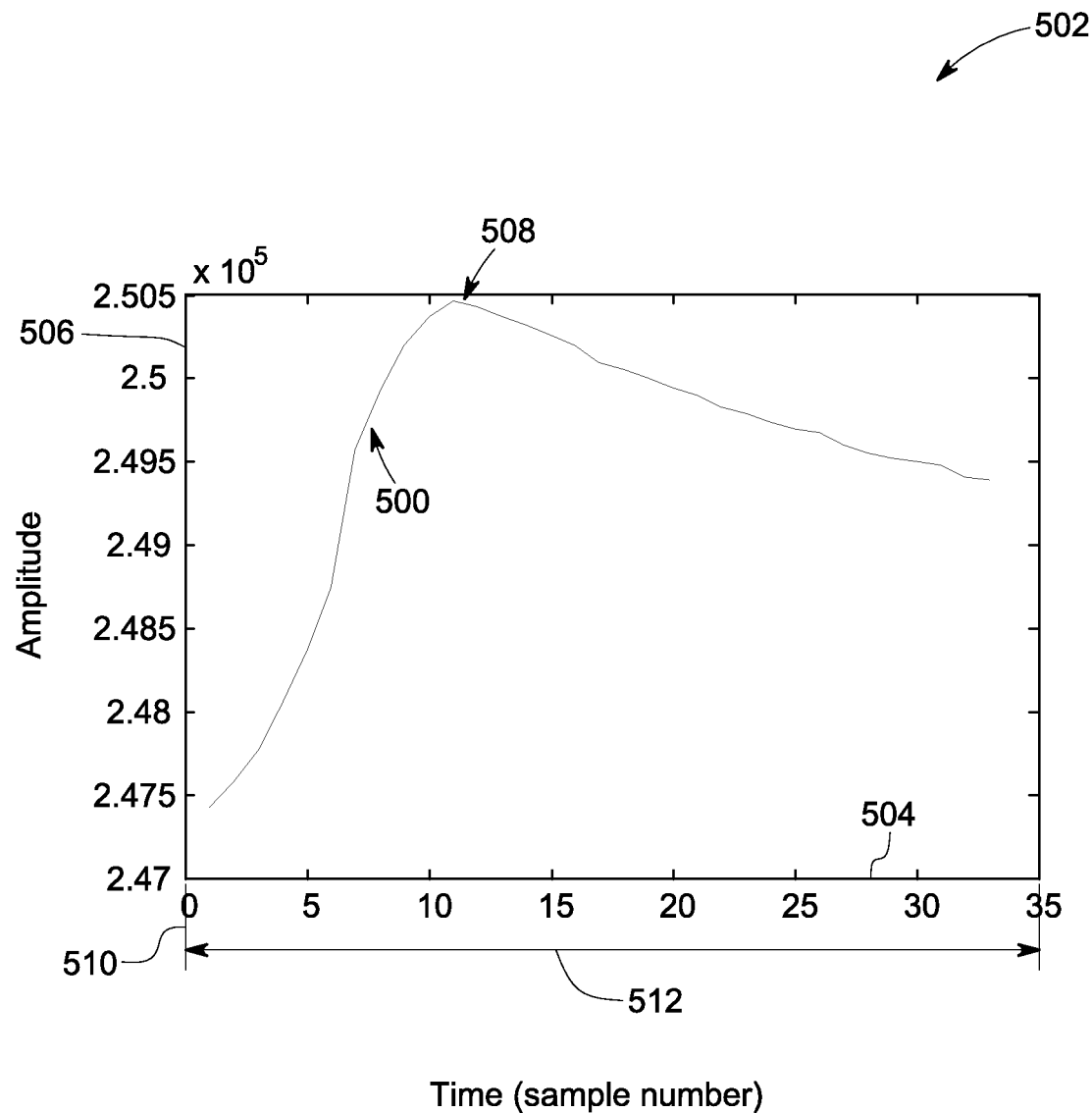

FIG. 5 is a graph representative of a portion of a first cardiac cycle 502 of a plethysmograph waveform, corresponding to a first duration 512 in accordance with another exemplary embodiment. The x-axis 504 is representative of time and the y-axis 506 is representative of the amplitude. A first start time 510 corresponds to "zero" value on the x-axis 504 and the first duration 512 corresponds to the entire x-axis 504. In the illustrated embodiment, the identified portion is a portion of a systolic waveform 500 of the first cardiac cycle 502. The graph includes a peak amplitude 508 and does not include an initial portion of the systolic waveform 500.

Figure 6:
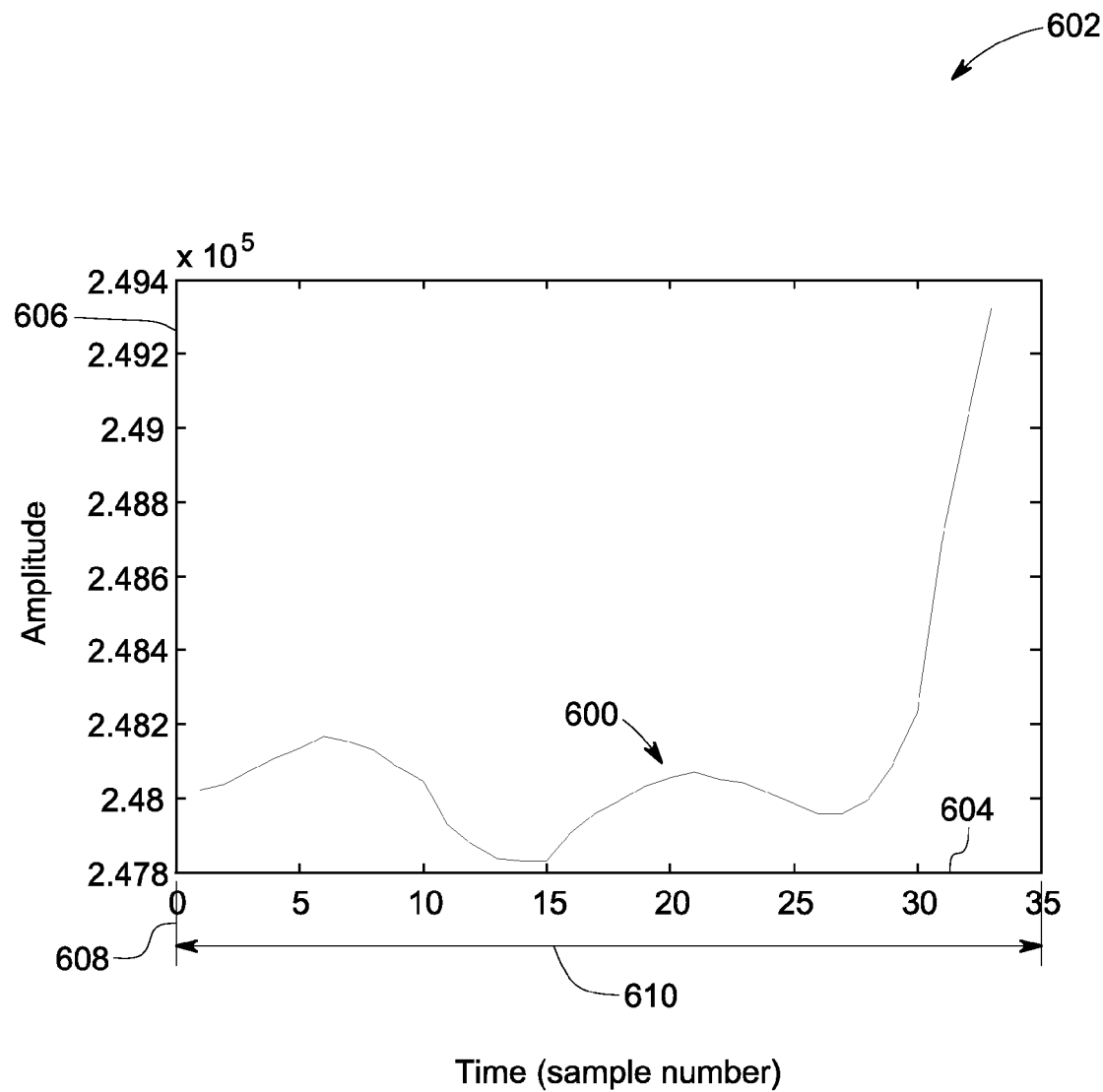

FIG. 6 is a graph representative of a portion of a first cardiac cycle 602 of a plethysmograph waveform, corresponding to a first duration 610 in accordance with another exemplary embodiment. The x-axis 604 is representative of time and the y-axis 606 is representative of amplitude. A first start time 608 corresponds to "zero" value on the x-axis 604 and the first duration 610 corresponds to the entire x-axis 604. The identified portion is an initial portion of a systolic waveform 600 of the first cardiac cycle 602. The graph does not include a peak amplitude of the systolic waveform 600.

In the embodiments of FIGS. 5 and 6, the identified portion of the first cardiac cycle includes a portion of the systolic waveform of the first cardiac cycle. The identified portion of the first cardiac cycle occurs within and beyond the systolic rise duration. In such embodiments, a second value greater than the first duration is assigned to the second duration. The second value greater than the first duration facilitates sampling of the entire systolic waveform of the second cardiac cycle during the second duration.

Figure 7:
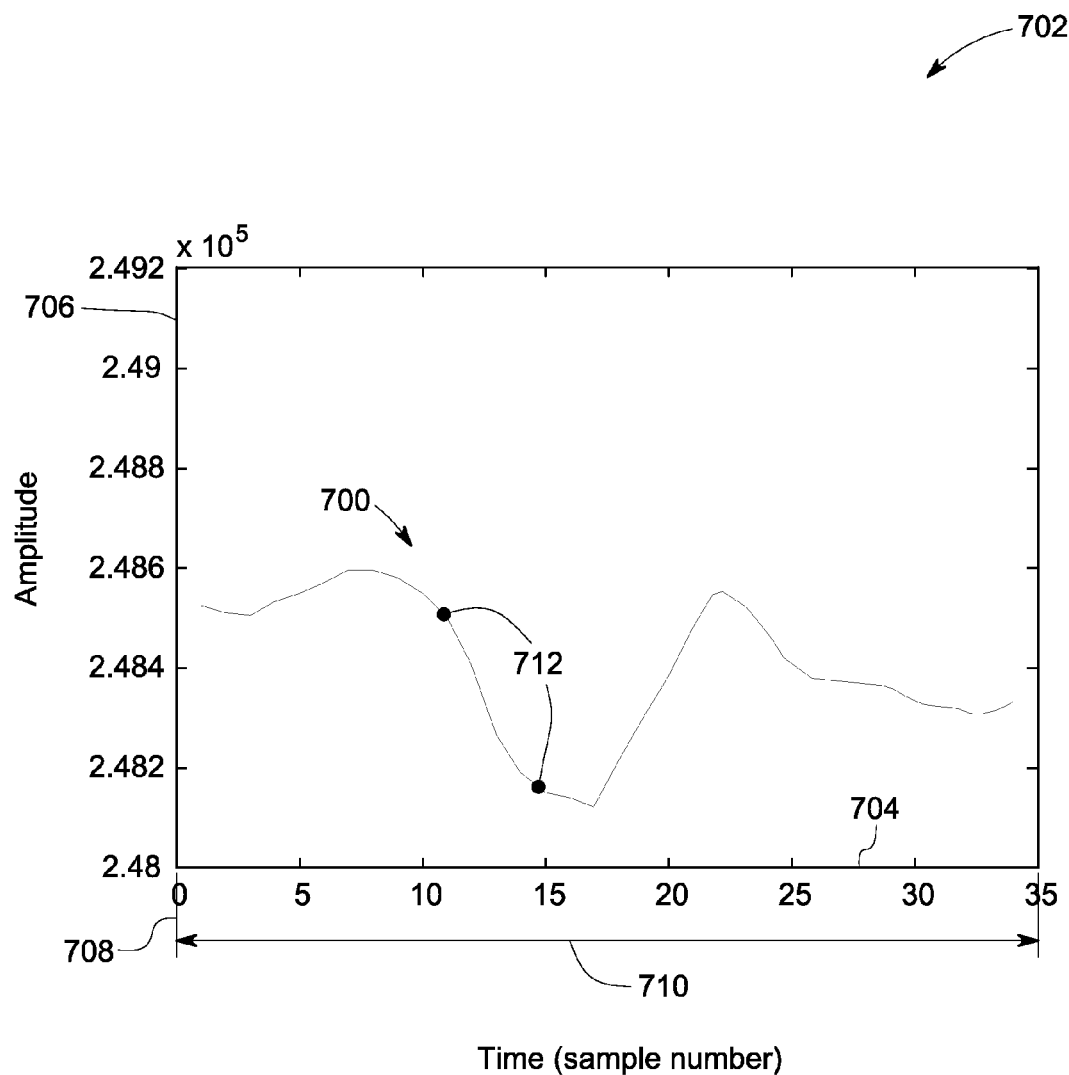

FIG. 7 is a graph representative of a portion of a first cardiac cycle 702 of a plethysmograph waveform, corresponding to a first duration 710 in accordance with another exemplary embodiment. The x-axis 704 is representative of time and the y-axis 706 is representative of amplitude. A first start time 708 corresponds to "zero" value on the x-axis 704 and the first duration 710 corresponds to the entire x-axis 704. The identified portion is a portion of a systolic waveform 700 of the first cardiac cycle 702 having a plurality of low amplitude values 712.

Figure 8:
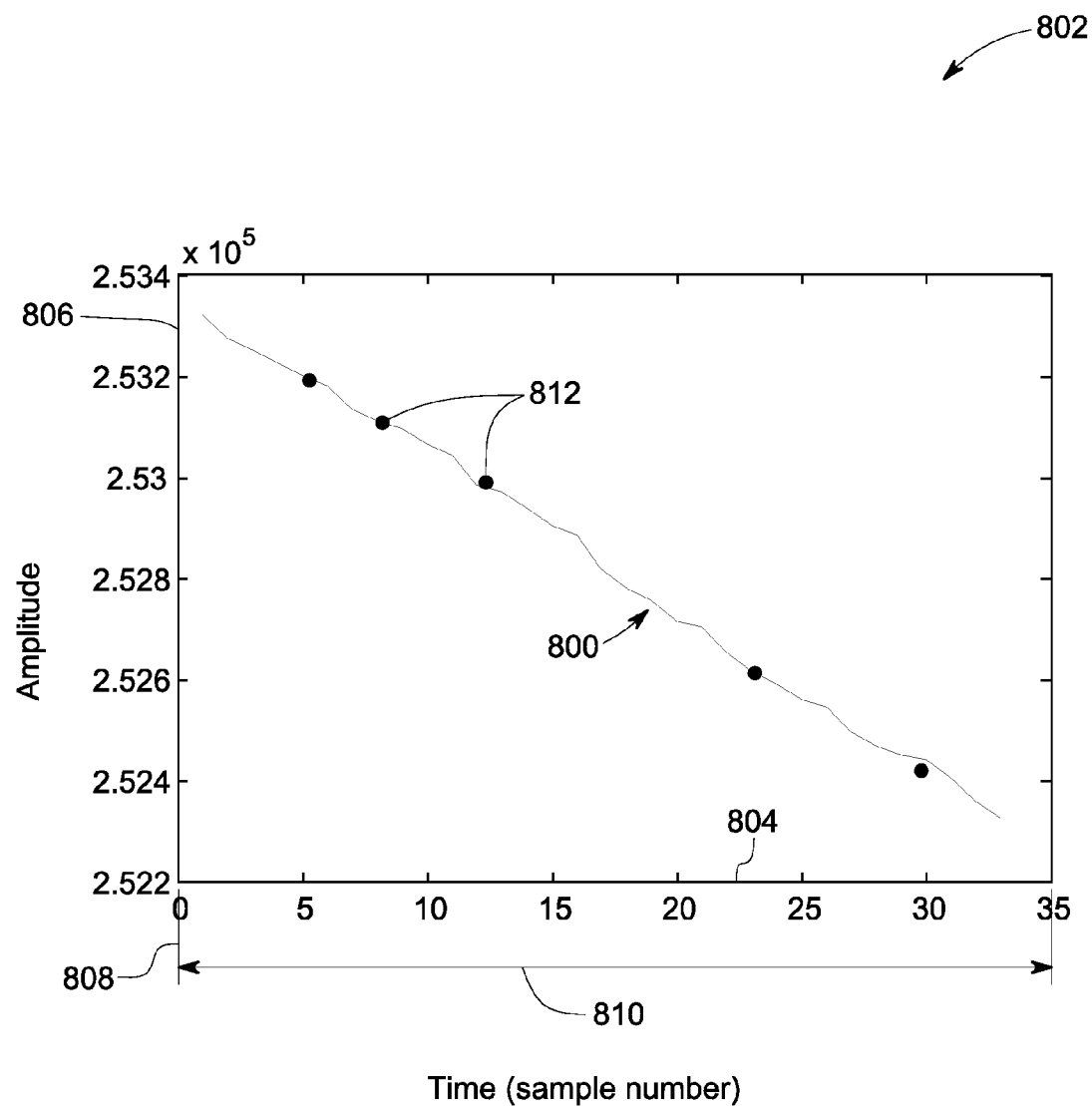

FIG. 8 is a graph representative of a portion of a first cardiac cycle 802 of the plethysmograph waveform, corresponding to a first duration 810 in accordance with another exemplary embodiment. The x-axis 804 is representative of time and the y-axis 806 is representative of amplitude. A first start time 808 corresponds to "zero" value on the x-axis 804 and the first duration 810 corresponds to the entire x-axis 802. The identified portion is a portion of a diastolic waveform 800 of the first cardiac cycle 802. The waveform 800 includes a plurality of amplitude values 812 which decrease with respect to time.

In the embodiments of FIGS. 7 and 8, the identified portion of the first cardiac cycle does not include a portion of the systolic waveform. In such embodiments, a third value equal to the entire duration is assigned to the second duration. Assigning the third value equal to the entire duration facilitates sampling of the entire cardiac cycle. The processing module is configured to determine the entire duration of the first cardiac cycle based on the plurality of amplitudes.

Figure 9:
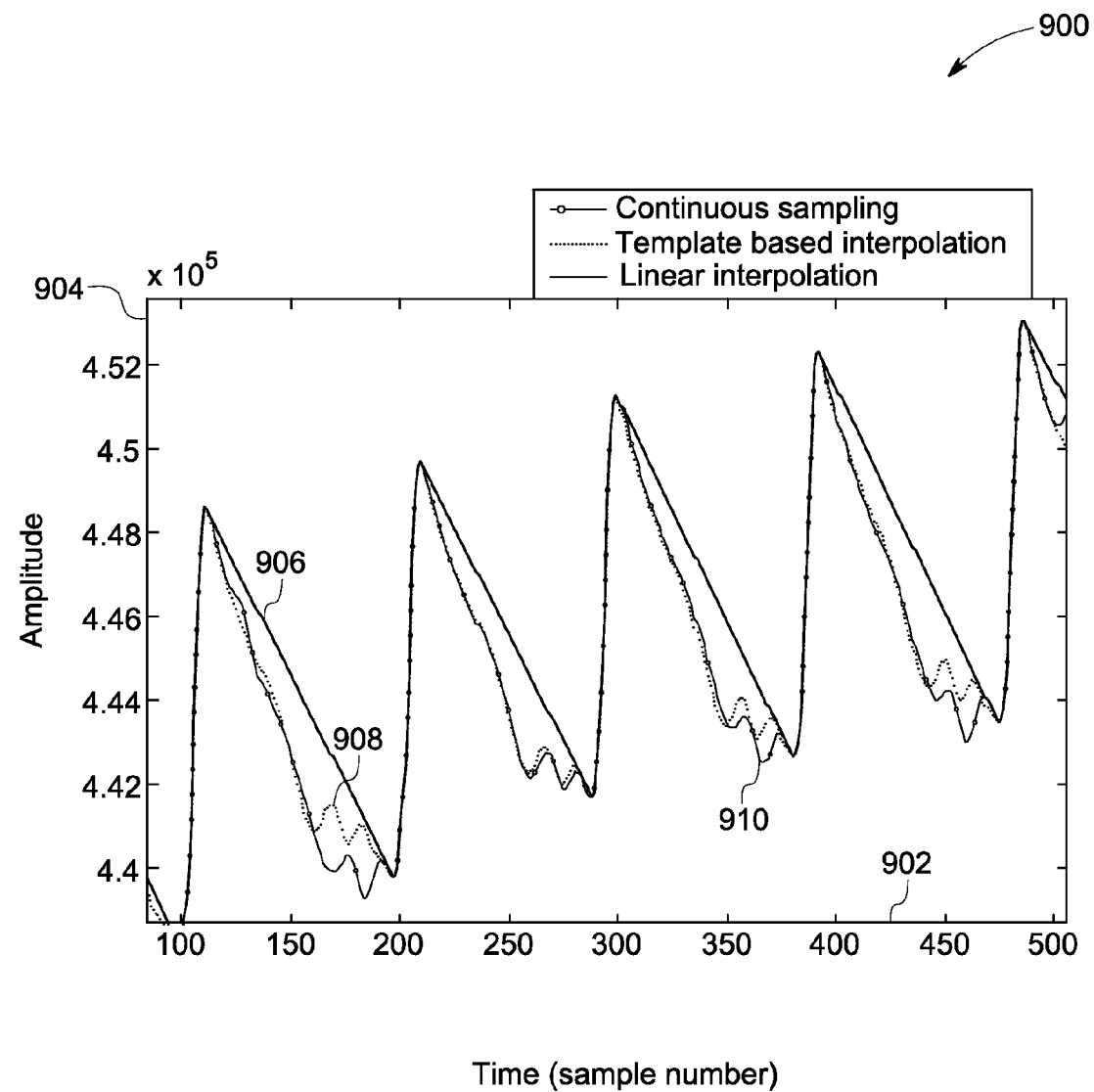
FIG. 9 is a graph representative of a plurality of plethysmograph waveforms obtained using reconstruction techniques in accordance with an exemplary embodiment.

FIG. 9 is a graph 900 representative of a plurality the plethysmograph waveforms obtained using reconstruction techniques in accordance with an exemplary embodiment. The x-axis 902 of the graph 900 is representative of time and the y-axis 904 is representative of amplitude. In an exemplary embodiment, a plurality of diastolic amplitudes corresponding to a diastolic waveform of a first cardiac cycle is determined using a linear interpolation technique. Linear interpolation technique involves determining diastolic amplitudes using a linear equation. In another embodiment, a plurality of diastolic amplitudes of a diastolic waveform of a first cardiac cycle is determined using a diastolic template. A mathematical model of the diastolic waveform is used as a diastolic template to determine the plurality of diastolic amplitudes. In the illustrated embodiment, a curve 908 is representative of a reconstructed cardiac waveform generated using an interpolation technique based on a diastolic template. In alternate embodiments, other mathematical methods such as logarithmic and polynomial based interpolation techniques may be used to generate the reconstructed cardiac waveform. A curve 910 is representative of a reconstructed cardiac waveform obtained by sampling both a systolic waveform and a diastolic waveform. It may be noted herein that the curve 908 is more proximate to the curve 910 compared to the proximity of the curve 906 with reference to the curve 910.

Figure 10:
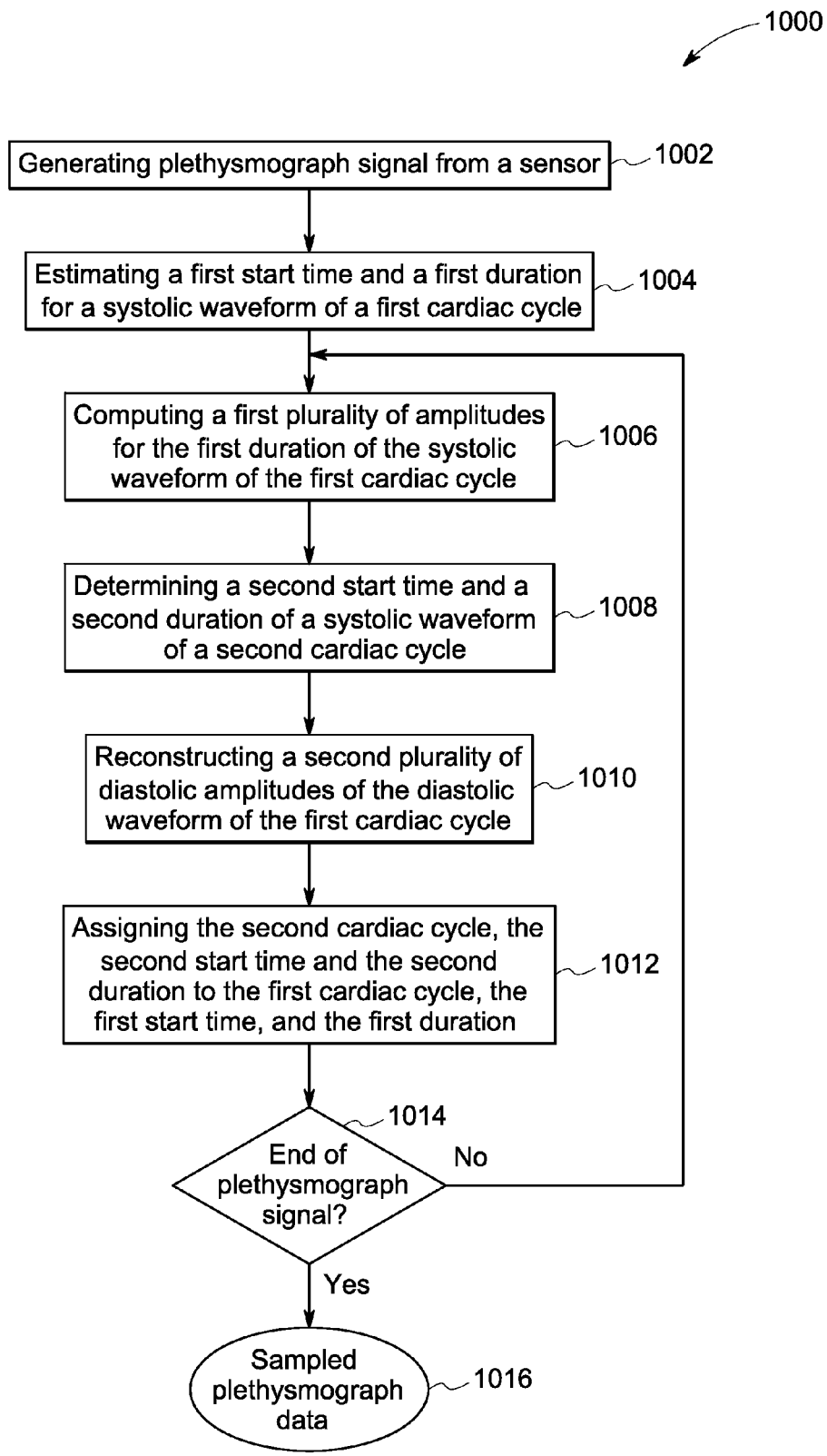
FIG. 10 is a flow chart illustrating a plurality of steps involved in low power sampling of plethysmograph signals in accordance with an exemplary embodiment.

FIG. 10 is a flow chart 1000 illustrating a plurality of steps involved in low power sampling of plethysmograph waveform in accordance with an exemplary embodiment. The method includes generating a plethysmograph waveform from a sensor 1002 indicative of a plurality of cardiac cycles. The plethysmograph waveform includes a systolic waveform and a diastolic waveform, corresponding to each cardiac cycle. A first start time and a first duration of the systolic waveform of a first cardiac cycle are estimated 1004 based on at least one cardiac cycle from the plurality of cardiac cycles. The first start time and the first duration are determined based on an average value of the plurality of cardiac cycles. A plurality of amplitudes is computed 1006 at a plurality of time instants of the first duration of the systolic waveform of the first cardiac cycle. A second start time and a second duration of the systolic waveform of a second cardiac cycle are determined 1008 based on the plurality of amplitudes. It should be noted herein that the second cardiac cycle is generated after the first cardiac cycle in time sequence. The plurality of amplitudes is processed to identify a portion of the first cardiac cycle which occurs within the first duration.

A plurality of diastolic amplitudes of the diastolic waveform of the first cardiac cycle is determined 1010 based on a reconstruction technique. The reconstruction technique, in one embodiment, includes determining the plurality of diastolic amplitudes using a diastolic template. In another embodiment, the reconstruction technique includes determining the plurality of diastolic amplitudes using a linear interpolation technique or a polynomial interpolation technique. The second cardiac cycle, the second start time, and the second duration are assigned 1012 to the first cardiac cycle, the first start time, and the first duration respectively. The method further includes checking generation of additional plethysmograph waveform 1014 and initiating an iterative operation if the additional plethysmograph waveform is available for processing. The iterative operation involves determining plurality of amplitudes, a second start time, and a second duration, and then reconstructing a plurality of diastolic amplitudes. The iterative operation is performed for the plurality of cardiac cycles generated sequentially in time to generate a sampled plethysmograph data 1016.

Figure 11:
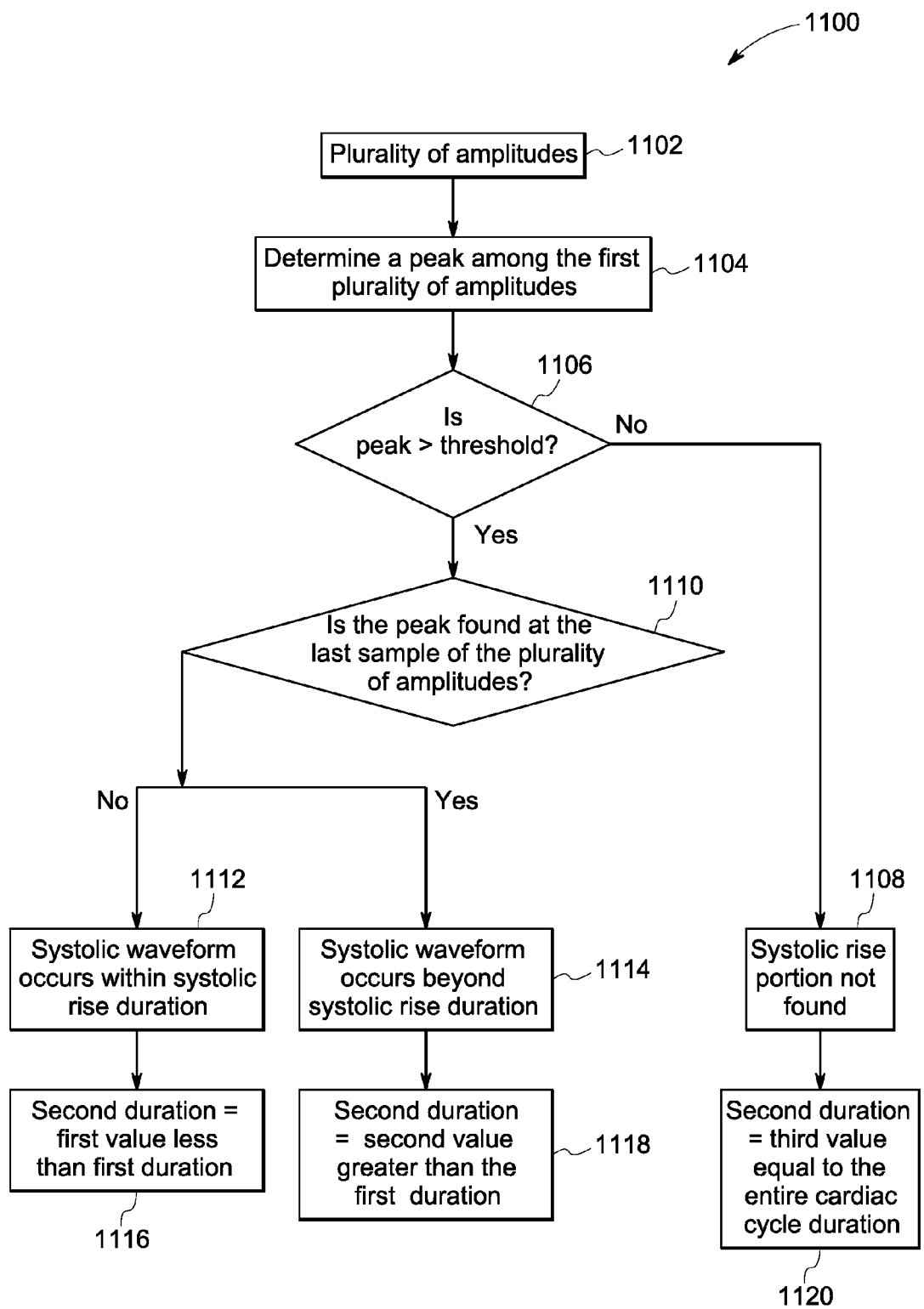
FIG. 11 is a flow chart illustrating a plurality of steps involved in determining a second duration of a systolic waveform of a second cardiac cycle among a plurality of cardiac cycles in accordance with an exemplary embodiment.

FIG. 11 is a flow chart 1100 illustrating a plurality of steps involved in determining a second duration in accordance with an exemplary embodiment. The method includes obtaining a plurality of amplitudes 1102 as discussed previously with reference to the flow chart of FIG. 10. A peak value is determined 1104 based on the plurality of amplitudes. In one exemplary embodiment, a plurality of derivative values of the plurality of amplitude values are determined by determining a difference of successive sample values of the plurality of amplitudes. The plurality of derivative values may exhibit "jitter peaks". The term "jitter peaks" is referred to herein as a plurality of peak values among the plurality of derivative values which are adjacent to each other. The jitter peaks are removed from the plurality of derivative values to generate a plurality of jitter-free derivative values. A maximum value among the plurality of jitter-free derivative values is determined as the peak value.

The determined peak value is compared with a threshold 1106 to determine the portion of the first cardiac cycle. In one embodiment, the threshold value is retrieved from the memory of the processor. In another embodiment, the threshold value is provided by the user. If the peak value is lesser than the threshold, the portion of the first cardiac cycle within the first duration is determined as a diastolic waveform 1108. If the peak value is greater than the threshold, the portion of the first cardiac cycle includes at least a portion of the systolic waveform. Further, a location of a sample value among the plurality of amplitudes, corresponding to the peak value is determined. The location of the sample value corresponding to the peak value is then analyzed 1110 to verify if the location of the sample value corresponds to the last sample of the plurality of amplitudes. If the sample having the peak value is the last sample among the plurality of amplitudes, the identified portion does not include the systolic waveform. The identified portion of the first cardiac cycle within the first duration includes a portion of the systolic waveform 1112. If the sample having the peak value is not the last sample among the plurality of amplitudes, the identified portion includes the systolic waveform. The identified portion of the first cardiac cycle within the first duration includes the systolic waveform 1114.

When the identified portion of the first cardiac cycle includes a portion of the systolic waveform, a first value greater than the first duration is assigned to the second duration 1116. When the identified portion of the first cardiac cycle includes the systolic waveform, a second value less than the first duration is assigned to the second duration 1118. When the identified portion of the first cardiac cycle includes a portion of the diastolic waveform, a third value equal to the duration of the cardiac cycle is assigned to the second duration 1120.

When the identified portion of the first cardiac cycle includes the systolic waveform, one time instant among the plurality of time instants, corresponding to a start of the systolic rise duration is determined. The determined time instant is assigned to the second start time.

Exemplary embodiments disclosed herein disclose a sampling technique for generating a sampled plethysmograph data with minimum power requirements. The systolic waveform of the cardiac cycle is sampled and the diastolic waveform is reconstructed based on the plurality of amplitudes of the systolic waveform. The emitters are powered only during a systolic rise period, thereby reducing the power requirement.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

What is claimed as new and desired to be protected by Letters Patent of the United States is:

1. A method comprising:
   (I) measuring a plethysmograph waveform using a sensor coupled to a peripheral artery of a subject, indicative of a plurality of cardiac cycles, wherein the plethysmograph waveform includes a systolic waveform and a diastolic waveform, corresponding to each cardiac cycle;
   (II) estimating a first start time and a first duration for the systolic waveform of a first cardiac cycle, based on at least one cardiac cycle from the plurality of cardiac cycles;
   (III) computing a plurality of amplitudes at a plurality of time instants for the first duration of the systolic waveform of the first cardiac cycle, wherein the sensor is powered only during the first duration to reduce consumption of power by the sensor;
   (IV) determining a second start time and a second duration of the systolic waveform of a second cardiac cycle from the plurality of cardiac cycles based on the plurality of amplitudes; wherein the second cardiac cycle is acquired after the first cardiac cycle in time sequence;
   (V) assigning the second cardiac cycle, the second start time, and the second duration to the first cardiac cycle, the first start time, and the first duration respectively; and
   iteratively performing (III), (IV), (V) for the plurality of cardiac cycles acquired sequentially in time to generate sampled plethysmograph data.

2. The method of claim 1, further comprising determining an average value of the plurality of cardiac cycles and estimating the first start time and the first duration based on the average value.

3. The method of claim 1, wherein the first duration comprises a systolic rise duration, a first offset duration before the systolic rise duration and a second offset duration after the systolic rise duration.

4. The method of claim 3, wherein the determining further comprises identifying a portion of the first cardiac cycle, which occurs within the first duration.

5. The method of claim 4, wherein the identifying comprises determining a peak value of the plurality of amplitudes.

6. The method of claim 5, wherein the determining further comprises assigning a first value less than the first duration, to the second duration, when the identified portion of the first cardiac cycle occurs within the systolic rise duration.

7. The method of claim 6, wherein the determining further comprises assigning a second value greater than the first duration, to the second duration, when the identified portion of the first cardiac cycle occurs within and beyond the systolic rise duration.

8. The method of claim 7, further comprising determining an entire duration of the first cardiac cycle.

9. The method of claim 8, wherein the determining further comprises assigning a third value equal to the entire duration, to the second duration, when the identified portion of the first cardiac cycle is the diastolic waveform.

10. The method of claim 3, wherein the determining comprises determining the second start time based on one time instant among the plurality of time instants, corresponding to a start time of the systolic waveform of the first cardiac cycle.

11. The method of claim 1, wherein the peripheral artery is located in a finger, or a toe, or a ear, or a nose, or a forehead, or other tissue sites of the subject.

12. A system comprising:
   a sensor coupleable to a peripheral artery of a subject and configured to measure a plethysmograph waveform indicative of a plurality of cardiac cycles, wherein the plethysmograph waveform includes a systolic waveform and a diastolic waveform corresponding to each cardiac cycle;
   a timing circuitry communicatively coupled to the sensor and configured to estimate a first start time and a first duration for the systolic waveform of a first cardiac cycle, based on at least one cardiac cycle from the plurality of cardiac cycles, wherein the sensor is powered only during the first duration to reduce consumption of power by the sensor;
   a sampling hardware module communicatively coupled to the timing circuitry and the sensor, wherein the sampling hardware module is configured to compute a plurality of amplitudes at a plurality of time instants for the first duration of the systolic waveform of the first cardiac cycle; and
   a microprocessor communicatively coupled to the sampling hardware module and the timing circuitry, wherein the microprocessor is configured to:
   (I) receive the plurality of amplitudes from the sampling hardware module;
   (II) determine a second start time and a second duration of the systolic waveform of a second cardiac cycle from the plurality of cardiac cycles, based on the plurality of amplitudes; wherein the second cardiac cycle is generated after the first cardiac cycle in time sequence;
   (III) assign the second cardiac cycle, the second start time, and the second duration to the first cardiac cycle, the first start time, and the first duration respectively; and
   iteratively perform (I), (II), (III) for the plurality of cardiac cycles generated sequentially in time to capture sampled plethysmograph data.

13. The system of claim 12, wherein the timing circuitry is further configured to determine an average value of the plurality of cardiac cycles and estimate the first start time and the first duration based on the average value.

14. The system of claim 13, wherein the microprocessor is configured to identify a portion of the first cardiac cycle, which occurs within the first duration.

15. The system of claim 14, wherein the microprocessor is further configured to determine a peak value of the plurality of amplitudes.

16. The system of claim 15, wherein the microprocessor is further configured to assign a first value less than the first duration, to the second duration, when the identified portion of the first cardiac cycle occurs within a systolic rise duration of the first duration.

17. The system of claim 16, wherein the microprocessor is configured to assign a second value greater than the first duration, to the second duration, when the identified portion of the first cardiac cycle occurs within and beyond the systolic rise duration.

18. The system of claim 17, wherein the microprocessor is configured to determine an entire duration of the first cardiac cycle.

19. The system of claim 18, wherein the microprocessor is configured to assign a third value equal to the entire duration, to the second duration, when the identified portion of the first cardiac cycle is the diastolic waveform.

20. The system of claim 16, wherein the microprocessor is configured to determine the second start time based on one time instant among the plurality of time instants, corresponding to a start time of the systolic waveform of the first cardiac cycle.

21. The system of claim 12, further comprising a reconstruction hardware module communicatively coupled to the sampling hardware module configured to generate a plurality of diastolic amplitudes corresponding to the diastolic waveform of the first cardiac cycle.

22. The system of claim 12, wherein the peripheral artery is located in a finger, or a toe, or a ear, or a nose, or a forehead, or other tissue sites of the subject.

23. A method comprising:
(I) generating a plethysmograph waveform using a sensor coupled to a peripheral artery of a subject, indicative of a plurality of cardiac cycles, wherein the plethysmograph waveform includes a systolic waveform and a diastolic waveform, corresponding to each cardiac cycle;
(II) estimating a first start time and a first duration for the systolic waveform of a first cardiac cycle, based on at least one cardiac cycle from the plurality of cardiac cycles;
(III) computing a plurality of systolic amplitudes at a plurality of time instants for the first duration of the systolic waveform of the first cardiac cycle, wherein the sensor is powered only during the first duration to reduce consumption of power by the sensor;
(IV) determining a second start time and a second duration of the systolic waveform of a second cardiac cycle from the plurality of cardiac cycles based on the first plurality of systolic amplitudes; wherein the second cardiac cycle is generated after the first cardiac cycle in time sequence;
(V) reconstructing a plurality of diastolic amplitudes corresponding to the diastolic waveform of the first cardiac cycle based on the plurality of systolic amplitudes;
(VI) assigning the second cardiac cycle, the second start time, and the second duration to the first cardiac cycle, the first start time, and the first duration respectively; and
iteratively performing (III), (IV), (V), (VI) for the plurality of cardiac cycles generated sequentially in time to generate sampled plethysmograph data.

24. The method of claim 23, wherein the reconstructing comprises determining the plurality of diastolic amplitudes using a diastolic template.

25. The method of claim 23, wherein the reconstructing comprises determining the plurality of diastolic amplitudes using a polynomial interpolation technique.

26. The method of claim 23, wherein the peripheral artery is located in a finger, or a toe, or a ear, or a nose, or a forehead, or other tissue sites of the subject.

27. A non-transitory computer readable medium encoded with a program to instruct at least one processor based device to:
(I) generate a plethysmograph waveform using a sensor coupled to a peripheral artery of a subject, indicative of a plurality of cardiac cycles, wherein the plethysmograph waveform includes a systolic waveform and a diastolic waveform, corresponding to each cardiac cycle;
(II) estimate a first start time and a first duration for the systolic waveform of a first cardiac cycle, based on at least one cardiac cycle from the plurality of cardiac cycles;
(III) compute a plurality of amplitudes at a plurality of time instants for the first duration of the systolic waveform of the first cardiac cycle, wherein the sensor is powered only during the first duration to reduce consumption of power by the sensor;
(IV) determine a second start time and a second duration of the systolic waveform of a second cardiac cycle from the plurality of cardiac cycles based on the plurality of amplitudes;
wherein the second cardiac cycle is generated after the first cardiac cycle in time sequence;
(V) assign the second cardiac cycle, the second start time, and the second duration to the first cardiac cycle, the first start time, and the first duration respectively; and
iteratively perform (III), (IV), (V) for the plurality of cardiac cycles generated sequentially in time to generate sampled plethysmograph data.

28. The non-transitory computer readable medium of claim 27, wherein the peripheral artery is located in a finger, or a toe, or a ear, or a nose, or a forehead, or other tissue sites of the subject.

* * * * *